(12) United States Patent
Bouali et al.

(10) Patent No.: US 6,462,211 B1
(45) Date of Patent: Oct. 8, 2002

(54) 4-HALOGENATED STEROIDS, THEIR PREPARATION PROCESS AND INTERMEDIATES, THEIR USE AS MEDICAMENTS AND THE PHARMACEUTICAL COMPOSITIONS CONTAINING THEM

(75) Inventors: Yamina Bouali, Villejuif (FR); Francois Nique, Le Perreux sur Marne (FR); Jean-Georges Teutsch, Pantin (FR); Patrick Van De Velde, Paris (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/746,245

(22) Filed: Dec. 22, 2000

Related U.S. Application Data

(62) Division of application No. 09/402,705, filed as application No. PCT/FR98/00709 on Apr. 8, 1998, now Pat. No. 6,239,121.

(30) Foreign Application Priority Data

Apr. 9, 1997 (FR) .............................................. 97 04321
Apr. 8, 1998 (WO) ................................ PCT/FR98/00709

(51) Int. Cl.$^7$ .............................. C07J 1/00; C07J 17/00; C07J 43/00
(52) U.S. Cl. ....................... 552/643; 552/623; 552/625; 540/107; 540/114
(58) Field of Search .................................. 540/107, 114, 540/28; 552/643, 623, 625

*Primary Examiner*—Barbara P. Badio
(74) *Attorney, Agent, or Firm*—Bierman, Muserlian and Lucas

(57) ABSTRACT

A subject of the invention is the compounds of formula (I):

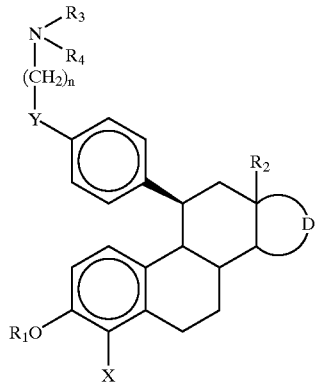

in which X is a halogen atom, D represents the remainder of an optionally substituted pentagonal or hexagonal ring and optionally carrying an unsaturation, $R_1$, $R_2$, $R_3$, $R_4$, Y and n are as defined in the description, their preparation process and intermediates, their use as medicaments and the compositions containing them.

3 Claims, No Drawings

4-HALOGENATED STEROIDS, THEIR PREPARATION PROCESS AND INTERMEDIATES, THEIR USE AS MEDICAMENTS AND THE PHARMACEUTICAL COMPOSITIONS CONTAINING THEM

This application is a division of U.S. patent application Ser. No. 09/402,705 filed Nov. 29, 1999, now U.S. Pat. No. 6,239,121, which is a 371 of PCT/FR98/00709 filed Apr. 8, 1998.

The present invention relates to 4-halogenated steroid compounds, their preparation process, their use as medicaments and the pharmaceutical compositions containing them.

Osteoporosis is a pathology which is characterized by a quantitative and qualitative reduction in bone matter, sufficient to lead to vertebral or peripheral fractures, in a spontaneous fashion or on occasions due to minimal traumas. Although this illness has many factors at its origin, it is the menopause which in women constitutes the dominating factor in bone loss or osteopenia.

This osteopenia manifests itself by a rarefaction and modification of the architecture of the spongy bone, the consequence of which is to increase the fragility of the skeleton and the risk of fractures. Bone loss increases strongly after the menopause due to the suppression of ovarian function and reaches 3 to 5% per year before slowing down after 65 years old.

For a therapeutic purpose, the post-menopause hormonal deficiency can be compensated for by a hormone replacement therapy where oestrogen plays a major role in preserving the bone mass. Jin et al (Steroids, Vol. 60 (1995) pp. 515–518 and Anstead et al (Steroids, Vol. 62 (1996) pp. 268–303) describe estradiol derivatives showing affinity to the estradiol receptor. But long-term oestrogenotherapy is sometimes accompanied by undesirable effects on the genital apparatus (endometrial hyperplasia, breast tumors . . . ), which constitutes a major drawback and limits its use.

It is therefore convenient to find compounds other than oestradiol having a dissociated oestrogen activity, namely an oestrogen activity at the bone level, while having no or little endometrial hyperplasia activity, nor breast tumor proliferation activity.

Therefore, a subject of the invention is the compounds of general formula (I):

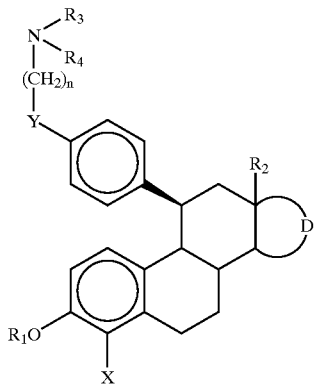

(I)

in which:
$R_1$ represents a hydrogen atom, a $(CH_2)_m$—Ar, (CO)—Ar, $(CH_2)_m$—Alk or (CO)—Alk radical,
$R_2$ represents a radical derived from a linear or branched, saturated or unsaturated hydrocarbon containing 1 to 6 carbon atoms D represents the remainder of a pentagonal or hexagonal ring optionally substituted and optionally carrying an unsaturation,
X represents a halogen atom,
Y is chosen from O, S, SO, $SO_2$ and NH,
n is an integer varying from 2 to 8,
either $R_3$ and $R_4$, identical or different, represent a hydrogen atom, a $(CH_2)_m$—Ar, $(CH_2)_m$—Het or $(CH_2)_m$Alk group,
or $R_3$ and $R_4$ form together with the atom of nitrogen to which they are linked an aromatic or non-aromatic, saturated or unsaturated mono- or polycyclic heterocycle with 3 to 15 members optionally containing 1 to 3 additional heteroatoms chosen from oxygen, sulphur and nitrogen, non-substituted or substituted,
Ar representing a carbocyclic aryl group containing 6 to 18 carbon atoms, Het representing a radical derived from a saturated or unsaturated aromatic or non-aromatic heterocycle containing 1 to 9 carbon atoms and 1 to 5 heteroatoms chosen from oxygen, nitrogen or sulphur atoms, Alk representing a radical derived from a saturated or unsaturated, linear, branched or cyclic, non-aromatic hydrocarbon and containing 1 to 12 carbon atoms, the Ar, Het or Alk radicals being able to be substituted or non-substituted, m represents 0, 1, 2 or 3, as well as their addition salts with bases or acids.

By halogen is meant: iodine, bromine, chlorine or fluorine.

By $(CH_2)_m$ is meant the following values: single bond in the case where m is equal to 0, $CH_2$, $(CH_2)_2$ and $(CH_2)_3$.

By the term Ar representing the carbocyclic aryl group containing 6 to 18 carbon atoms, is meant a derivative of an aromatic cyclic hydrocarbon such as the phenyl, naphthyl, phenanthrenyl radical or a derivative of a condensed, bicyclic or tricyclic hydrocarbon containing a benzene ring such as indanyl, indenyl, dihydronaphthyl, tetrahydronaphthyl or fluorenyl. The junction is carried out at the level of the benzene ring. Preferably it is phenyl.

By the term (Het) representing a radical derived from a saturated or unsaturated, aromatic or non aromatic heterocycle containing 1 to 9 carbon atoms and 1 to 5 heteroatoms chosen from oxygen, nitrogen and sulphur atoms, the following are designated in particular:
heterocyclic monocyclic radicals, for example thienyl, furyl, pyrannyl, pyrrolyl, imidazolyl, pyrazolyl, pyridyl, pyrazinyl, pyrimidinyl, pyridazinyl, thiazolyl, oxazolyl, furazannyl, pyrrolinyl, imidazolinyl, pyrazolinyl, thiazolinyl, triazolyl, tetrazolyl radicals,
condensed heterocyclic rings, for example benzofuranyl, benzothienyl, benzimidazolyl, benzothiazolyl, naphtho [2,3-b]thienyl, thianthrenyl, isobenzofuranyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, beta-carbolinyl, acridinyl, phenazinyl, phenothiazinyl, phenoxazinyl, indolinyl, isoindolinyl, imidazopyridyl, imidazopyrimidinyl or also condensed polycyclic systems constituted by heterocyclic moncyclics as defined above such as for example furo[2,3-b]pyrrole or thieno[2,3-b]furan,
or saturated heterocycles such as pyrrolidine, piperidine, morpholine.

By the term (Alk) representing a radical derived from a saturated or unsaturated, linear, branched or cyclic non-aromatic hydrocarbon, is designated in the case of acyclic hydrocarbons the alkyl radicals such as methyl, ethyl, propyl, isopropyl, butyl, isobutyl, tert-butyl, n-pentyl, n-hexyl, 2-methyl pentyl, 2,3-dimethyl butyl, n-heptyl, 2-methylhexyl, 2,2-dimethylpentyl, 3,3-dimethylpentyl, 3-ethylpentyl, n-octyl, 2,2-dimethylhexyl, 3,3-dimethylhexyl 3-methyl-3ethylpentyl, nonyl, 2,4-dimethylheptyl or n-decyl, the alkenyl radicals such as vinyl, propenyl, isopropenyl, allyl, 2-methylallyl, butenyl or isobutenyl, or the alkynyl radicals such as ethynyl, propynyl, propargyl, butynyl or isobutynyl, and in the case of cyclic radicals, the cycloalkyl radicals, such as cyclopropyl, cyclobutyl, cyclopentyl or cyclohexyl.

It will preferably be methyl and ethyl radicals. By CO—Alk is preferably meant $COCH_3$ and COET, by CO—Ar is preferably meant the benzoyl radical, when m is different from zero, $(CH_2)_m$—Ar will preferably be the benzyl group.

When $R_3$ and $R_4$ form together with the nitrogen atom to which they are linked a heterocycle, it is in particular mono- or bicyclic heterocycles optionally containing another heteroatom chosen from oxygen and nitrogen such as the following unsaturated heterocycles: pyrrolyl, imidazolyl, indolyl, pyridyl, pyrazinyl, pyrimidinyl, pyridazinyl, thiazolyl, oxazolyl, furazolinyl, pyrazolinyl, thiazolinyl, or, more particularly, the following saturated heterocycles:

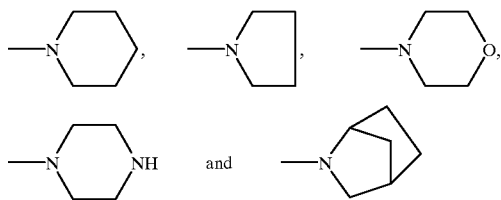

When the different Alk, Ar, Het groups, as well as the remainder of a pentagonal or hexagonal ring mentioned above, are substituted, they can in particular be substituted by the following radicals:

halogen, namely fluorine, chlorine, bromine or iodine, alkoxy such as methoxy, ethoxy, propyloxy, isopropyloxy, butyloxy, alkylthio such as methylthio, ethylthio, propylthio, isopropylthio, butylthio, amino, alkylamino such as methylamino or ethylamino, dialkylamino such as dimethylamino, diethylamino, methylethylamino, each of these dialkylamino radicals being optionally in oxidized form, aminoalkyl such as aminomethyl or aminoethyl, dialkylaminoalkyl such as dimethylamino methyl or ethyl, dialkylaminoalkyloxy such as dimethylamino ethyloxy, hydroxyl optionally acylated, acyl such as acetyl, propionyl, butyryl, benzoyl, free, esterified carboxy such as alkoxy carbonyl for example methoxy carbonyl or ethoxy carbonyl, cyano, trifluoromethyl, aryl such as phenyl, aralkyl such as benzyl, alkyl, alkenyl or alkynyl these radicals being themselves optionally substituted by the halogen, alkyl, alkoxy, alkylthio, aminoalkyl or dialkylamino radicals indicated above.

Of course, the expression "substituted" indicates that one or more identical or different substituents can be present. In the case of (Het), the substituents can be at the level of the NH or carbon atom.

Of course the values of $R_1$, $R_2$, $R_3$ and $R_4$, are independent of each other.

The invention naturally extends to the salts of the compounds of formula (I), such as for example the salts formed with mineral or organic acids on the amine. It can then be one of the following acids: hydrochloric, hydrobromic, nitric, sulphuric, phosphoric, acetic, formic, propionic, benzoic, maleic, fumaric, succinic, tartaric, citric, oxalic, glyoxylic, aspartic, alkane sulphonics such as methane or ethane sulphonics, arylsulphonics, such as benzene or para-toluene sulphonics and arylcarboxylics. When the compounds of formula (I) contain an acid function, the invention extends to the salts of alkali metals, alkaline earth or ammonium, optionally substituted.

A more particular subject of the invention is the compounds of general formula (I) as defined above in which (D) represents the remainder of a pentagonal ring of formula:

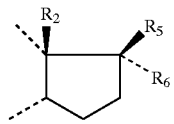

in which $R_2$ retains the same meaning as previously, either $R_5$ represents an OH, O—$(CH_2)_m$—Alk, O—(CO)—Alk, O—$(CH_2)_m$—Ar, O—(CO)—Ar, O—$(CH_2)_m$—Het, O—(CO)—Het radical and $R_6$ represents a hydrogen atom, an alkyl, alkenyl or alkynyl radical containing 1 to 6 carbon atoms substituted or non substituted, m, Alk, Ar and Het being as defined previously, or $R_5$ and $R_6$ form together with the carbon atom which carries them one of the following rings:

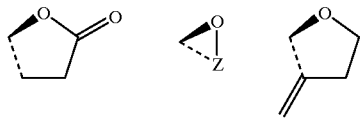

in which z represents a —$(CH_2)_1$— or —CH=CH—$(CH_2)_1'$ group; 1 being an integer comprised between 1 and 4 and 1' being an integer equal to 1 or 2, or $R_5$ and $R_6$ form together an oxo group or NOH, as well as their addition salts with acids or bases.

A quite particular subject of the invention is the compounds of formula (I) as defined previously corresponding to general formula (I'):

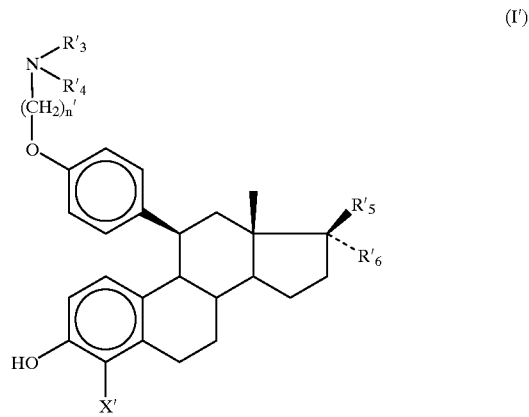

(I')

in which:

X' represents a chlorine or bromine atom n' is comprised between 2 and 5, either R'₃ and R'₄, identical or different, represent an alkyl radical containing 1 to 6 carbon atoms or R'₃ and R'₄ form together with the nitrogen atom to which they are linked, a saturated mono- or polycyclic remainder with 3 to 15 members optionally containing an additional heteroatom chosen from oxygen, sulphur and nitrogen, R'₅ and R'₆ have the same meaning as R₅ and R₆, as well as their addition salts with acids and bases.

A quite particular subject of the invention is the compounds of formula (I) as defined previously corresponding to general formula (I') in which:

either R'₅ represents an OH radical and R'₆ represents a hydrogen atom, an alkyl, alkenyl or alkynyl radical containing 1 to 6 carbon atoms, substituted or non-substituted, or R'₅ and R'₆ form together with the carbon atom that carries them one of the following rings:

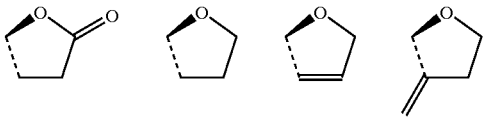

or R'₅ and R'₆ form together an oxo group, as well as their addition salts with acids or bases.

A quite particular subject of the invention is the, compounds of formula (I) corresponding to general formula (I') as defined previously in which:

X' represents a chlorine atom n' is equal to 2, either R'₃ and R'₄, identical or different, represent an alkyl radical containing 1 to 6 carbon atoms or R'₃ and R'₄ form together with the nitrogen atom the following saturated heterocycles:

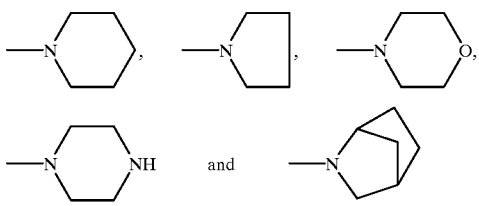

and either R'₅ represents an OH radical and R'₆ represents a hydrogen atom, an alkyl, alkenyl or alkynyl radical containing 1 to 6 carbon atoms, substituted or non substituted, or R'₅ and R'₆ form together with the carbon atom which carries them one of the following rings:

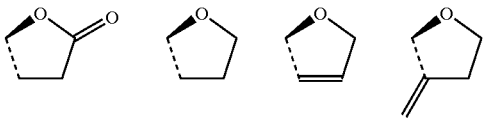

or R'₅ and R'₆ form together an oxo group, as well as their addition salts with acids or bases.

A quite particular subject of the invention is the compounds of formula (I) as well as their addition salts with acids the names of which follow:

4-chloro-3-hydroxy-11β-[4-[2-(diethylamino)ethoxy]phenyl]-estra-1,3,5(10)-trien-17-one, 4-chloro-3-hydroxy-11β-[4-[2-(dimethylamino)ethoxy]phenyl]-estra-1,3,5(10)-trien-17-one, 4-chloro-3-hydroxy-11β-[4-[2-(1-piperidinyl)ethoxy]phenyl]-estra-1,3,5(10)-trien-17-one, 4-chloro-3-hydroxy-11β-[4-[2-(1-pyrrolidinyl)ethoxy]phenyl]-estra-1,3,5(10)-trien-17-one, 4-bromo-3-hydroxy-11β-[4-[2-(1-piperidinyl)ethoxy]phenyl]-estra-1,3,5(10)-triene-17-one, 4-chloro-11β-[4-[2-(dimethylamino)ethoxy]phenyl]-estra-1,3,5(10)-triene-3,17beta-diol, 4-chloro-11β-[4-[2-(diethylamino)ethoxy]phenyl]-estra-1,3,5(10)-triene-3,17beta-diol, 4-chloro-11β-[4-[2-(1-piperidinyl)ethoxy]phenyl]-estra-1,3,5(10)-triene-3,17beta-diol, 4-bromo-11β-[4-[2-(1-piperidinyl)ethoxy]phenyl]-estra-1,3,5(10)-triene-3,17beta-diol, 4-chloro-11β-[4-[2-(1-pyrrolidinyl)ethoxy]phenyl]-estra-1,3,5(10)-triene-3,17beta-diol, 4-chloro-11β[-4-[2-(diethylamino)ethoxy]phenyl]-19-nor-17alpha-pregna-1,3,5(10)-triene-20-yne-3,17beta-diol, 4-chloro-11β-[4-[3-(1-piperidinyl)propoxy]phenyl]-estra-1,3,5(10)-triene-3,17beta-diol, 4-chloro-11β-[4-[4-(1-piperidinyl)butoxy]phenyl]-estra-1,3,5(10)-triene-3,17beta-diol, 4-chloro-11β-[4-[5-(1-piperidinyl)pentyloxy]phenyl]-estra-1,3,5 (10)-triene-3,17beta-diol, gamma lactone of (17alpha)-4-chloro-3,17beta-dihydroxy-11β-[(4-[2-(diethylamino)ethoxy]phenyl]-19-nor-pregna-1,3,5(10)-triene-21-carbdxylic acid, gamma lactone of (17alpha)-4-chloro-3,17beta-dihydroxy-11β [4-[2-(1-pyrrolindinyl)ethoxy)phenyl]-19-nor-pregna-1,3,5 (10)-triene-21-carboxylic acid, gamma lactone of (17alpha)-4-chloro-3,17beta-dihydroxy-11β-[4-[2-(1-piperidinyl)ethoxy]phenyl]-19-nor-pregna-1,3,5(10)-triene-21-carboxylic acid, gamma lactone of (17alpha)-4-chloro-3,17beta-dihydroxy-11β-[4-[3-(1-piperldinyl)propoxy]phenyl]-19-nor-pregna-1,3,5(10)-triene-21-carboxylic acid, gamma lactone of (17alpha)-4-chloro-3,17beta-dihydroxy-11β-[4-[4-(1-piperidinyl)butoxy]phenyl]-19-nor-pregna-1,3,5(10)-triene-21-carboxylic acid, gamma lactone of (17alpha)-4-chloro-3,17beta-dihydroxy-11β-[4-[5-(1-piperidinyl)pentyloxy]phenyl]-19-nor-pregna-1,3,5(10)-triene-21-carboxylic acid, (17beta)-4-chloro-11β-[4-[2-(diethylamino)ethoxy]phenyl]-spiro[estra-1,3,5(10)-triene-17,2'(5'H)furan]-3-ol, (17beta)-4-chloro-11-[4-[2-(1-piperidinyl)ethoxy]phenyl]-spiro[estra-1,3,5(10)-triene-17,2'(5'H)furan]-3-ol, (17beta)-4-chloro-11β-[4-[2-(1-pyrrolidinyl)ethoxy]phenyl]-spiro[estra-1,3,5(10)-triene-17,2'(5'H)furan]-3-ol, (17beta)-4-chloro-4',5'-dihydro-11β-[4-[2-(1-piperidinyl)ethoxy]phenyl]-spiro[estra-1,3,5(10)-triene-17,2'(3'H)furan]-3-ol, (17beta)-4-chloro-11β-[4-[3-(1-piperidinyl)propoxy]phenyl]-spiro[estra-1,3,5(10)-triene-17,2'(5'H)furan]-3-ol, (17beta)-4-chloro-4',5'-dihydro-11β-[4-[3-(1-piperidinyl)propoxy]phenyl]-spiro[estra-1,3,5(10)-triene-17,2'(3'H)furan]-3-ol, (17beta)-4-chloro-11β-[4-[4-(1-piperidinyl)butoxy]phenyl]-spiro[estra-1,3,5(10)-triene-17,2'(5'H)furan]-3-ol, (17beta)-4-chloro-4',5'-dihydro-11β-[4-[4-(1-piperidinyl)-butoxy]phenyl]-spiro[estra-1,3,5(10)-triene-17,2'(3'H)furan]-3-ol, 4-chloro-11β-[4-[2-(diethylamino)ethoxy]phenyl]-17alpha-methyl-estra-1,3,5(10)-triene-3,17beta-diol, 4-chloro-17alpha-methyl-11β-[4-[2-(1-piperidinyl)ethoxy]phenyl]-estra-1,3,5(10)-triene-3,17beta-diol, Quite particularly a subject of the invention is also the compound of formula (I) as defined above, the name of which follows:

4-chloro-11β-[4-[2-(diethylamino)ethoxy]phenyl]-estra-1,3,5(10)-triene-3,17beta-diol, as well as its addition salts with acids.

A subject of the invention is also a preparation process for the compounds of general formula (I) as defined previously, characterized in that a compound of general formula (II):

(II)

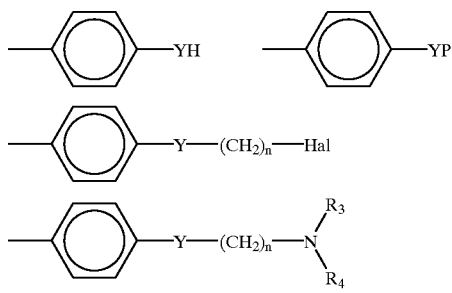

in which D and $R_2$ are as defined previously, $R_7$ represents one of the following groups:

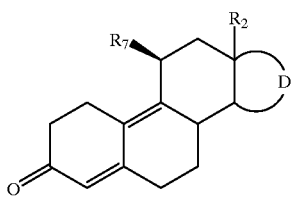

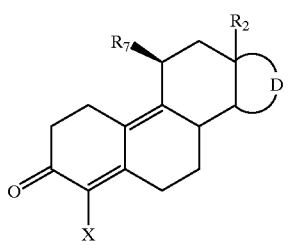

in which n, Y, $R_3$ and $R_4$ are as defined previously, P is a protective group, Hal represents a halogen, is subjected to the action of a halogenation reagent in order to obtain the compound of formula (III):

(III)

which is subjected to the action of an aromatization reagent of ring A, then to the action of a base in order to obtain the compound of formula (IV) corresponding to certain compounds of general formula (I):

(IV)

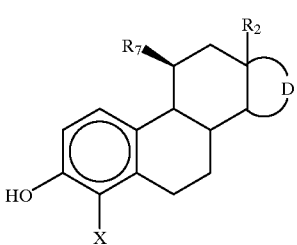

which compounds of formula (II), (III) or (IV) are subjected, if desired and if necessary, in an appropriate order, to one or more of the following reactions:

protection of the compounds in which $R_7$ is a —Ph—YH group, deprotection of the compounds in which $R_7$ is a Ph—YP group, the action of a compound of formula $Hal_1$—$(CH_2)_n$—$Hal_2$ on the compounds in which $R_7$ is a —Ph—YH group, $Hal_1$ or $Hal_2$ identical or different representing a halogen in order to obtain compounds in which $R_7$ is a —Ph—Y—$(CH_2)_n$—$Hal_2$ group, the action of a compound of formula $R_3$—NH—$R_4$ on the compounds in which $R_7$ is a Ph—Y—$(CH_2)_n$—$Hal_2$ group, in order to obtain compounds in which $R_7$ is a Ph—Y—$(CH_2)_n$—$NR_3R_4$ group, the action of a halide salt (M—$Hal_3$) on the compounds in which $R_7$ is a Ph—Y—$(CH_2)_n$—$Hal_2$ group in order to obtain the compounds in which $R_7$ is a —Ph—Y—$(CH_2)_n$—$Hal_3$ group, protection of the OH group in position 3 or 17, deprotection of the OH group in position 3 or 17, alkylation of the OH group in position 3 or 17, acylation of the OH group in position 3 or 17, the action of a reducing agent when D represents the remainder of a pentagonal ring as defined previously and $R_5$ and $R_6$ together form an oxo group, the action of an organometallic on the compounds of formula (IV) with D representing the remainder of a pentagonal ring as defined previously and $R_5$ and $R_6$ together forming an oxo group, the action of a lactonization agent on the compounds of formula (IV) with D representing the remainder of a pentagonal ring as defined previously and $R_5$ and $R_6$ forming together an oxo group, the action of a reducing agent of the double bond, when D represents the remainder of a pentagonal ring as defined previously and $R_5$ and $R_6$ form together with the carbon that carries them, an O—$(CH_2)_{n'}$—CH=CH— group, the action of a reducing agent of the double bond, when D represents the remainder of a pentagonal ring as defined previously, and $R_6$ is an alkenyl or alkynyl radical containing 2 to 6 carbon atoms, halogenation in position 4, then aromatization of ring A, of the compound of general formula (II), aromatization of ring A of the compound of formula (III), salification.

The action of a halogenation reagent such as N-bromosuccinimide or N-chlorosuccinimide on the compounds of formula (II) is carried out in particular in the presence of a dipolar aprotic solvent such as dimethylformamide.

The aromatization reaction followed by the saponification reaction (action of the base) is carried out according to standard methods as described in the European Patent 0097572. A mixture of acetic anhydride and acetyl bromide is preferably used as the aromatization agent then a base such as soda in methanol as the saponification agent.

The protection and deprotection reactions are standard methods known to a person skilled in the art. A fairly complete review is found in the following work: Protective groups in organic synthesis T. W Greene, John Wiley & Sons (1981).

The protective group P preferably represents an alkyl radical containing 1 to 4 carbon atoms, a benzyl group, an $R_C R_D R_E Si$ group, in which $R_C$, $R_D$ and $R_E$, identical or different, independently of each other each represent an alkyl radical containing 1 to 4 carbon atoms or a phenyl group. Quite particularly it is the $Si(Me)_2CMe_3$ or $—Si(Ph)_2CMe_3$ groups.

As an example, the deprotection reactions of the compounds of formula (II), (III) or (IV) with $R_7$=Ph—OP or the compounds of formula (IV) the 3-OH of which is protected (3-OP), when P is a methyl radical, can be carried out by the action of tribromobdrane in dichloromethane or hydrochloric acid in pyridine, the deprotection reactions when P is a benzyl group can be carried out by the action of hydrogen in the presence of palladium on carbon in ethyl acetate or by the action of trifluoroacetic acid, the deprotection reactions when P is a tertbutyldiphenylsilyl group can be carried out by the action of tetrabutyl ammonium fluoride in solution in tetrahydrofuran.

When P is a tetrahydropyrannyl group, the deprotection is carried out in the presence of an aqueous acid in an alcoholic solvent and preferably by the action of hydrochloric acid in methanol.

The action of a compound of formula $Hal_1—(CH_2)_n—Hal_2$ on a compound of formula (II), (III) or (IV) in which $R_7$=Ph—YH can be carried out, in particular when Y=O, in the presence of a base in a solvent such as acetone.

The action of a compound of formula $R_3—NH—R_4$ on the compounds in which $R_7$ is a $Ph—Y—(CH_2)_n—Hal_2$ group is carried out under standard conditions for the substitution of nucleophiles, in particular in the presence of an aprotic solvent such as tetrahydrofuran.

The substitution reaction of a halogen by another when in particular $R_7$ is a $Ph—Y—(CH_2)_n—Cl$ group is preferably carried out by the action of NaI in methyl-ethylketone.

The alkylation or acylation reactions of the OH group in position 3 or 17 are carried out by standard methods known to a person skilled in the art.

The reduction of 17-keto into the corresponding alcohol ($R_5$=OH and $R_6$=H) is carried out according to standard methods, in particular by the action of an alkaline borohydride such as sodium borohydride in methanol or ethanol or by the action of aluminium and lithium tetrahydride.

The action of an organometallic on 17-keto allows access to the products of formula (IV) in which D represents the remainder of a pentagonal ring as defined previously, $R_5$ is a hydroxyl and $R_6$ represents an optionally substituted alkyl, alkenyl, alkynyl radical.

The organometallic derivative of an alkyl, alkenyl or alkynyl is chosen from the magnesium compounds of formula AlkMgHal and the lithium compounds of formula AlkLi in which Alk represents an alkyl, alkenyl or alkynyl group containing at most 8 carbon atoms, Hal represents a halogen atom. In a preferred method of implementing the process, Hal represents a chlorine, bromine or iodine atom, preferably bromine. The reaction preferably takes place in the presence of cerium chloride. In a preferred method for implementing the process, Hal represents a chlorine, bromine or iodine atom, preferably bromine. The lactonization reaction from 17 keto is carried out according to the method of STURTZ (ref: G. STURTZ and J-J. YAOUANC, Synthesis, (1980), 289) in particular in the presence of alkyl bisdimethylamidophosphate in the presence of an alkyl-lithium compound such as n-butyllithium in tetrahydrofuran.

The total or partial reduction reaction when $R_6$ is an alkenyl or alkynyl or when $R_5$ and $R_6$ form together with the carbon that carried them an $O—(CH_2)_{m'}—CH=CH—$ group, can be carried out either in a total manner by the action of hydrogen in the presence of a catalyst such as palladium on carbon or a rhodium catalyst such as Wilkinson's reagent or in a partial manner (alkynyl becomes alkenyl) by the action of a poisoned catalyst such as palladium on barium sulphate poisoned with pyridine or triethylamine.

The esterification and salification reactions are carried out by current methods known to a person skilled in the art.

A more particular subject of the invention is a preparation process for the compounds of general formula (I') as described previously characterized in that a compound of general formula compound (II'):

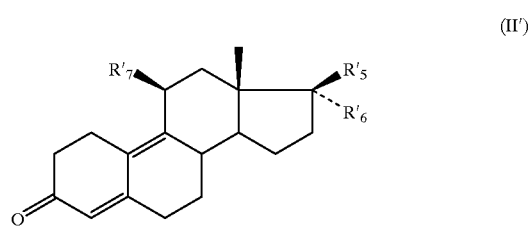

(II')

in which $R'_5$ and $R'_6$ are as defined previously, $R'_7$ represents:

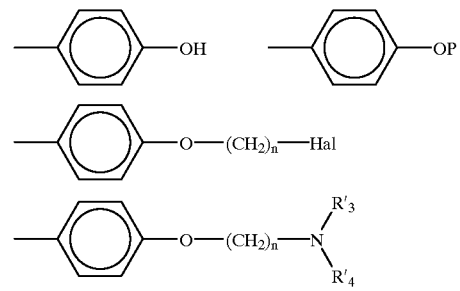

is subjected to the action of a halogenation reagent in order to obtain the compound of formula (III'):

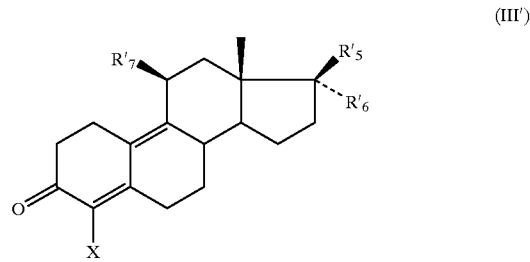

(III')

which is subjected to the action of an aromatization reagent of ring A, then to the action of a base in order to obtain the compound of formula (IV') corresponding to certain compounds of general formula (I'):

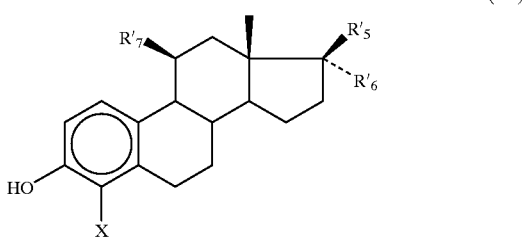

which compounds of formula (II'), (III') or (IV'), are subjected, if desired and if necessary, in an appropriate order, to one or more of the following reactions:

protection of the compounds in which $R'_7$ is a —Ph—OH group, deprotection of the compounds in which $R'_7$ is a Ph—OP group, the action of a compound of formula $Hal_1$—$(CH_2)_n$—$Hal_2$ on the compounds in which $R'_7$ is a —Ph—OH group, $Hal_1$ or $Hal_2$, identical or different, representing a halogen in order to obtain the compounds in which $R_7$ is a —Ph—O—$(CH_2)_n$—$Hal_2$ group, the action of a compound of formula $R'_3$—NH—$R'_4$ on the compounds in which $R'_7$ is a Ph—O—$(CH_2)_n$—$Hal_2$ group, in order to obtain the compounds in which $R'_7$ is a Ph—O—$(CH_2)_n$—$NR'_3R'_4$ group, the action of a halide salt (M—$Hal_3$) on compounds in which $R'_7$ is a Ph—O—$(CH_2)_n$—$Hal_2$ group in order to obtain the compounds in which $R_7$ is a —Ph—O—$(CH_2)_n$—$Hal_3$ group, protection of the OH group in position 3 or 17, deprotection of the OH group in position 3 or 17, alkylation of the OH group in position 17, acylation of the OH group in position 17, the action of a reducing agent when $R'_5$ and $R'_6$ together form an oxo group, the action of an organometallic on the compounds of formula (IV') with $R'_5$ and $R'_6$ together forming an oxo group, the action of a lactonization agent on the compounds of formula (IV') with $R'_5$ and $R'_6$ together forming an oxo group, the action of a reducing agent of the double bond, when $R'_5$ and $R'_6$ form together with the carbon which carries them, an O—$(CH_2)_1$—CH=CH— group, the action of a reducing agent of the double bond, when $R'_6$ is an alkenyl or alkynyl radical containing 2 to 6 carbon atoms, halogenation in position 4, then aromatization of ring A, of the compound of formula (II'), aromatization of the compound of formula (III'), salification.

The compounds of general formula (I) as well as their addition salts with pharmaceutically acceptable acids have oestrogen, anti-oestrogen and anti-proliferative activities.

Therefore the compounds of formula (I) can be used in the treatment of disorders linked to hypofolliculinia, for example, amenorrheas, dysmenorrheas, repeated abortions, premenstrual disorders, in the treatment of certain oestrogen-dependent pathologies such as prostatic adenomas or carcinomas, mammary carcinomas and their metastases or in the treatment of benign breast tumors, as an anti-uterotrophic as well as in the replacement treatment for the menopause or the perimenopause.

Among the symptoms and consequences linked to the menopause are more specifically meant hot flushes, sweats, vaginal atrophy and dryness, urinary symptoms and in the long term a reduction in bone mass and an increased risk of fractures, and the loss of the cardiovascular protection provided by the oestrogens.

In particular, the compounds of formula (I) and their addition salts with pharmaceutically acceptable acids or bases can be used in the prevention or the treatment of osteoporosis.

The compounds of formula (I) and their addition salts with pharmaceutically acceptable acids can also be used for the prevention or the treatment of osteoporosis in man.

They can also be used for the prevention or the treatment of secondary osteoporoses (for example cortisonal, linked with immobilization).

The compounds of formula (I) and their addition salts with pharmaceutically acceptable acids or bases in particular have a dissociated oestrogenic activity.

By dissociated oestrogenic activity is meant an oestrogenic activity at bone level while demonstrating only minimal activity at uterine level, thus not entailing an endometrial proliferation (much lower activity than that of oestradiol).

Furthermore, the compounds according to the invention have the following advantages:

They have an anti-oestrogenic activity at the level of the breast. Unlike oestradiol, they do not stimulate the growth of human mammary tumor cells and can even inhibit their growth. The compounds according to the invention are therefore particularly advantageous for the treatment of the menopause in women at risk from breast cancer (family antecedents) who are therefore excluded from a replacement treatment using oestradiol.

They can also be used in the treatment of breast cancers.

They lead to a lowering of the seric cholesterol level to a level equivalent to that induced by oestradiol. Therefore, they strengthen cardiovascular protection.

Finally, as the compounds according to the invention have no oestrogen activity at the uterine level, they do not require to be administered in combination with a progestomimetic compound.

A subject of the invention is thus compounds of general formula (I) as well as their addition salts with pharmaceutically acceptable acids or bases, as medicaments.

A more particular subject of the invention is compounds of formula (I) and their addition salts with pharmaceutically acceptable acids or bases as medicaments used for the prevention or the treatment of osteoporosis.

The invention extends to the pharmaceutical compositions containing at least one of the medicaments defined above as active ingredient.

The compounds of formula (I) are used by digestive, parenteral or local route, for exemple by percutaneous route. They may be prescribed in the form of plain or coated tablets, capsules, granules, suppositories, pessaries, injectable preparations, ointments, creams, gels, microspheres, implants, intravaginal rings, patches, which are prepared according to the usual methods.

The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The useful dose varies as a function of the illness to be treated and the administration route; it can vary for example from 1 to 1000 mg per day for an adult by oral route. Patent 0057115.

The compounds of general formula (II) or (II') with

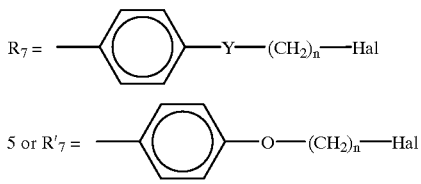

can also be formed from the compounds of formula (IIa):

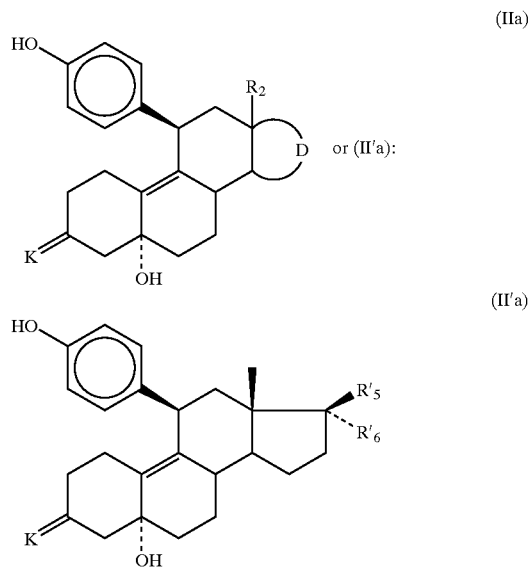

in which D, $R_2$, $R'_5$ and $R'_6$ are as defined previously and K represents a protective group of the ketone function, which is subjected to the action of an O-alkylation reagent of formula Hal—$(CH_2)_n$—Hal then to the action of a dehydration reagent which is equally capable of releasing the ketone.

The compounds of formula (IIa) or (II'a) are also known compounds and described in the following patent:

U.S. Pat. No. 5,043,332.

A subject of the invention is also, as intermediate products, the compounds of formulae (III), (III'), (IV) and (Iv').

The examples below illustrate the invention without however limiting it.

Solvents described in the examples: AcOEt (ethyl acetate), TEA (triethylamine), $CH_2Cl_2$ (dichloromethane), $CHCl_3$ (chloroform), MeOH (methanol), $NH_4OH$ (ammonium hydroxide), iPrOH (isopropyl alcohol).

EXAMPLE 1

4-chloro-3-hydroxy-11beta-[4-[2-(1-piperidinyl) ethoxy]phenyl]-estra-1,3,5 (10)-trien-17-one Stage A: 11beta-[4-(2-bromoethoxy)phenyl]-estra-4,9-diene-3,17-dione a) O-alkylation 8.0 g of 5α-hydroxy-11β-(4-hydroxy-phenyl)-estr-9-en-3,17-dione cyclic 3-(1,2-ethanediyl acetal) is dissolved under an inert atmosphere in 80 ml of 99% 1,2-dibromomethane, 21 ml of 50% soda, 0.800 g of tetrabutyl ammonium bromide, and agitation is carried out under reflux for 1 hour.

b) Acid Hydrolysis 93 ml of 6M hydrochloric acid is added at ambient temperature, agitation is carried out for 45 minutes, followed by extraction, washing, drying and evaporating under pressure reduced until the crude product is obtained (m=13.17 g) which is recrystallized from a 50 ml of dichloromethane/50 ml of isopropyl ether mixture. 5.96 g+7.0 g of pure expected product is obtained (Rf $CH_2Cl_2$/ACOET 70/0=0.45). M.p.= 208° C.

IR ($CHCl_3$) 1735 $cm^{-1}$: 17 keto; 1658 and 1609 $cm^{-1}$: conjugated ketone; 1583 and 1509: aromatic.

Stage B: 11beta-[4-(2-bromoethoxy)phenyl]-4-chloro-estra-4,9-diene-3,17-dione (Introduction of cl in Position 4)

1.86 g of N-chlorosuccinimide is added to a solution, under inert atmosphere, at 60° C., of 5.025 g of the product obtained in Stage A, in 67 ml of dimethylformamide and agitation is carried out for 10 minutes. Salt water is added, followed by extraction, drying and evaporating under reduced pressure until the crude product is obtained (m=8.149 g) which is purified by chromatography on silica eluting with a cyclohexane/ethyl acetate mixture (60/40), 5.43 g of pure expected product is obtained (Rf essence G/AcOEt 60/40=0.35).

IR ($CHCl_3$) 1736 $cm^{-1}$: 17-keto; 1677 $cm^{-1}$: conjugated ketone; 1609, 1582, 1550 and 1509 $cm^{-1}$: C=C and aromatic.

Stage C: 11beta-[4-(2-bromoethoxy)phenyl]-4-chloro-3-hydroxy-estra-1,3,5,(10)triene-17-one a) Aromatization 4.7 ml of acetic anhydride and 4.7 ml of acetyl bromide is added, under an inert atmosphere, at ambient temperature to 4.7 g of the product obtained in Stage B in 50 ml of dichloromethane/siliporite, while cooling the reaction medium down and agitation is carried out for 5 hours 30 minutes.

b) Saponification of the Phenolic Acetate

After the dichloromethane is evaporated off under under reduced pressure and at ambient temperature, 47 ml of tetrahydrofuran is added under an inert atmosphere while cooling down the reaction medium, the 47 ml of methanol then 47 ml of soda are added, agitation is carried out for 1 hour at ambient temperature. After acidification with hydrochloric acid, extraction is carried out followed by washing, drying and evaporating under pressure reduced until the crude product is obtained (m=4.84 g) which is purified by chromatography on silica eluting with a cyclohexane/ethyl acetate mixture (70/30). 4.37 g of expected product is obtained (Rf=essence G/ACOET 70/30=0.18).

IR ($CHCl_3$). 3537 $cm^{-1}$: phenolic-OH; 1733 $cm^{-1}$: 17-keto; 1609, 1580, 1511 and 1481 $cm^{-1}$: aromatic.

Stage D: 4-chloro-3-hydroxy-11beta-[4-(2-iodoethoxy) phenyl]-estra-1,3,5(10)trien-17-one (Iodization)

2.44 g of sodium iodide is added under an inert atmosphere, at ambient temperature, to a solution of 4.11 g of the brominated derivative prepared in Stage C in 80 ml of methylethyl ketone, and agitation is carried out overnight under reflux. Water is added followed by extraction, drying and evaporating under reduced pressure until 4.184 g of expected crude product is obtained (Rf=methanol/water (90/10)=0.30).

Stage E: 4-chloro-3-hydroxy-11beta-[4-[2-(1-piperidinyl) ethoxy]phenyl]-estra-1,3,5(10)trien-17-one (Substitution of the Iodine by Piperidine)

1.248 g of the iodized derivative obtained in Stage D, is dissolved under inert atmosphere, at ambient temperature in 25 ml of tetrahydrofuran/siliporite and 1.35 ml of piperidine is added and the reaction medium is heated under reflux for 1 hour 30 minutes. After evaporation of the tetrahydrofuran under reduced pressure at ambient temperature, water and ethyl acetate are added, followed by washing, drying and evaporation under reduced pressure until 1.185 g of the crude amino derivative is obtained which is purified by chromatography on silica eluting with with an ethyl acetate/triethylamine mixture 95/5. 1.039 g of expected pure product is obtained (Rf=ethyl acetate/TEA (95/5)=0.20).

NMR $CDCl_3$ 0.45 ppm (s): $CH_3$ in position 18; 2.48 ppm: cyclic —$CH_2$—N's, 2.71 ppm (t): $CH_2$—N of the chain; 3.99 ppm (t): $CH_2$—OAr; 3.99 ppm: $H_{11}$; 6.63 ppm: $H_2$; 6.81 ppm: $H_1$; 6.60.ppm: Ar—O; 6.91 ppm: Ar—C.

EXAMPLE 2

4-chloro-3-hydroxy-11beta-[4-[2-(1-pyrrolidinyl) ethoxy]phenyl]-estra-1,3,5(10)-trien-17-one The operation is carried out as in Example 1 Stage E, but starting with 6 g of the iodized derivative obtained in Stage of Example 1, 60 ml of tetrahydrofuran/siliporite and 4.6 ml of pyrrolidine. 4.2 g of expected pure product is obtained (Rf: ACOET/TEA (80/20)=0.24).

NMR ($CDCl_3$): 0.45 ppm (s): $CH_3$ in position 18; 1.78 ppm (m): $CH_2$ in beta position of N; 2.59 ppm (m): $CH_2$ in alpha position of N; 2.84 ppm (t): $CH_2$—N of the chain; 3.98 ppm (t): $CH_2$—OAr; 3.98 ppm (t): $H_{11}$, $CH_2$—O of the chain; 6,62 ppm: $H_2$; 6.81 ppm: $H_1$; 6.62 ppm: Ar—O; 6.91 ppm: Ar—C.

EXAMPLE 3

4-chloro-3-hydroxy-11beta-[4-[2-diethylamino) ethoxy]phenyl]-estra-1,3,5(10)-trien-17-one The operation is carried out as in Example 1 Stage E, but starting with 1.2 g of the iodized derivative obtained in Stage D of Example 1, 25 ml of tetrahydrofuran/siliporite and 1 ml of diethylamine.

0.688 g of expected pure product is obtained (Rf: ACOEt/TEA (95/5)=0.22).

NMR ($CDCl_3$): 0.45 ppm (s): $CH_3$ in position 18; 1.03 ppm (t): N—$CH_2$—$CH_3$; 2.60 ppm (q): N—$CH_2$—$CH_3$; 2.81 ppm (t): $CH_2$—N of the chain; 3.93 ppm (t): $CH_2$—OAr; 4.00 ppm (t): $H_{11}$; 6.63 ppm: $H_2$; 6.82 ppm: $H_1$; 6.63 ppm: Ar—C; 6.91 ppm: Ar—C.

EXAMPLE 4

4-bromo-3-hydroxy-11beta-[4-[2-(1-piperidinyl) ethoxy]phenyl]-estra-1,3,5(10)-trien-17-one
Stage A: 11beta-[4-(2-chloroethoxy)phenyl]-estra-4,9-diene-3,17-dione (O-alkylation)

(7.9 ml×2) 1-bromo-2-chloroethane followed by 6 ml of 50% soda and 500 mg of tetrabutylammonium bromide are added to a suspension of 5 g of 11beta-(4-hydroxyphenyl)-estra-4,9-diene-3,17-dione in 50 ml of acetone. The mixture is taken to reflux for 4 hours. Water is added followed by extracting, drying and evaporating under reduced pressure until a crude product is obtained which is purified in ether.

5.45 g of expected product is obtained (Rf $CH_2Cl_2$/acetone 90/10=0.82).

NMR ($CDCl_3$): 0.58 3H (s): $CH_3$ in position 18; 3.80 2H (t): $\underline{CH_2}$Cl; 4.28 2H (t): $\underline{CH_2}$O; 4.49 1H (d): $H_{11}$; 5.80 1H (s): $H_4$; 6.82 2H (d): 2H arom.; 7.08 2H (d): H arom.

Stage B: 4-bromo-11beta-[4-(2-chloroethoxy)phenyl]-estra-4,9-diene-3,17-dione (Introduction of Br in Position 4)

A solution of 2.43 g of NBromo succinimide is added under a nitrogen atmosphere to a suspension of 5.35 g of the product of Stage A in 70 ml of dimethylformamide. After agitation for 2 hours at ambient temperature, 200 ml of ethyl acetate and 400 ml of water saturated in NaCl are added followed by extraction, washing, drying and evaporating under reduced pressure until 8 g of crude product is obtained which is purified by chromatography eluting with a dichloromethane/acetone mixture 98/2. 4.66 g of expected pure product is obtained. (Rf $CH_2Cl_2$/acetone 95/5=0.92).

NMR ($CDCl_3$): 0.57 3H (s): $\underline{CH_3}$ in position 18; 3.25 1H (dt): $H_6$; 3.80 2H (t): $\underline{CH_2}$Cl; 4.20 2H (t): $\underline{CH_2}$O; 4.38 1H (d, wide): $H_{11}$; 7.07 and 6.83 4H: AA'BB' H arom.

Stage C: 4-bromo-11beta-[4-(2-chloro ethoxy)phenyl]-3-hydroxy-estra-1,3,5(10)-trien-17-one (Aromatization of Ring A)

The operation is carried out as in Stage C of Example 1, starting with 4.5 g of the product obtained in the preceding stage. 3.05 g of expected product is obtained. (Rf $CH_2Cl_2$/ACOET90/10=0.64).

NMR ($CDCl_3$): 0.45 3H (s): $CH_3$ in position 18; 3.75 2H (t): $\underline{CH_2}$Cl; 4.12 2H (t): $CH_2$O; 4.00 1H (t): $H_{11}$; 5.48 1H (s): OH; 6.93 and 6.64 2H: AA'BB' 4H arom; 6.85 and 6.64 2H (d): $H_1H_2$.

Stage D: 4-bromo-3-hydroxy-11beta-[4-(2-iodo ethoxy) phenyl]-estra-1,3,5 (10)-trien-17-one (Iodization)

The operation is carried out as in Stage D of Example 1, starting with 1 g of the product obtained in the preceding stage. 1.14 g of expected product is obtained.

Stage E: 4-bromo-3-hydroxy-11beta-[4-[2(1-piperidinyl) ethoxy]phenyl]-estra-1,3,5(10)-trien-17-one (Substitution of the Iodine by Piperidine)

The operation is carried out as in Stage E of Example 1 starting with 1.1 g of the product obtained in the preceding stage. 270 mg of expected pure product is obtained (Rf ACOET/TEA 90/10=0.43).

NMR ($CDCl_3$): 0.45 3H (s): $CH_3$ in position 18; 2.47 4H (m): cyclic $C\underline{H_2}$N; 2.70 2H (t): $C\underline{H_2}$—N; 3.98 2H (t): $C\underline{H_2}$—O; 3.98 1H (t wide): $H_{11}$; 6.88 and 6.62 2H (d): $H_1$ and $H_2$; 6.90 and 6.62 4H: AA'BB' H aromatic.

EXAMPLE 5

4-chloro-11beta-[4-[3-(1-piperidinyl)propoxy] phenyl]-estra-1,3,5(10)-triene-3,17-beta-diol
Stage A: 4-chloro-11beta-[4-(phenylmethoxy)phenyl]-estra-4,9-diene-3,17-dione (Chlorination Position 4)

5.295 g of N-chlorosuccinimide is added at 60° C. under an inert atmosphere to a solution of 13.6 g of 11β-[4-(phenylmethoxy)phenyl]-estra-4,9-diene-3,17-dione in 120 ml of dimethylformamide, agitation is carried out for 10 minutes then the reaction medium is poured into a saturated aqueous solution of NaCl, followed by extraction, washing, drying and evaporating under reduced pressure until the crude product is obtained (m=19.128 g). A second trial is carried out, the crude products are collected and purified by chromatography eluting with an ethyl acetate-cyclohexane mixture 30/70. 23.28 g of expected pure product is obtained. (Rf ACOET/cyclohexane 30/70=0.19).

NMR (CDCl$_3$): 0.58 (s): CH$_3$ in position 18; 3.25 (dt): 1H equatorial H$_6$; 4.39 (dl): H$_{11}$; 5.02 (s): CH$_2$Ph; 6.89: H in ortho position of Ph-O; 7.06: H in meta position of Ph-O; 7.29 to 7.45: aromatic H of CH$_2$—Ph.

Stage B: 4-chloro-3-[[(2,2-dimethylethyl)(diphenyl)silyl]oxy]11-beta-[4-(phenylmethoxy)phenyl]-estra-1,3,5(10)-trien-17-one (aromatization/saponification/blocking of the phenol)

a) Aromatization and Saponification

The operation is carried out as in Stage C of Example 1 starting with the product obtained in the preceding stage. 13.5 g of expected pure product is obtained (3-OH).

b) Blocking of the Phenol 13.5 g+5.6 g of the product obtained in the preceding stage, 191 ml of dichloro methane/siliporite, 14.5 ml of terbutyl diphenyl chlorosilane and 258 mg of 4-DMAP are dissolved under an inert atmosphere, and agitation is carried out for 23 hours under reflux. The reaction medium is then poured into water, extraction is carried out followed by washing, drying and evaporating under reduced pressure until 41.322 g of crude product is obtained in the form of an oil which is purified by chromatography elutino with an ethyl acetate/petroleum ether mixture 20/80 then 40/60. 1.275 g of expected pure product is obtained. (Rf ACOET/petroleum ether 20/80=0.27).

NMR (CDCl$_3$): 0.42 (s): CH$_3$ in position 18; 1.11 (s): C(CH$_3$)$_3$; 7.25 to 7.40–7.60 to 7.75 Si—Ph; 3.85 (t): H$_{11}$; 4.94 (s): CH$_2$—Ph; 6.65:: H in ortho position (Ph—O); 6.84: H in para position (Ph—O); 6.17 (d): H$_1$; 6.47 (d): H$_2$.

Stage C: 4-chloro-3-[[(2,2-dimethylethyl)(diphenyl)silyl]oxy]11-beta-[4-(hydroxyphenyl)-estra-1,3,5 (10)-trien-17-one (Deprotection (Debenzylation))

15.6 g of palladium hydroxide on magnesia and 40 ml of 1,4-cyclohexadiene are added, under an inert atmosphere, at ambient temperature to a suspension of 20.82 g of the product obtained in the preceding stage in 420 ml of methanol, then taken to reflux for 8 hours. After filtration and evaporation under reduced pressure, 22 g of crude product is obtained which is purified by chromatography eluting with a cyclohexane/ethyl acetate mixture 7/3. 19.4 g of expected pure product is obtained. (Rf cyclohexane/ACOET 7/3=0.27).

NMR (CDCl$_3$): 0.42 (s): CH$_3$ in position 18; 1.11 (s): C(CH$_3$)$_3$; 3.83 (tl): H$_{11}$; 4.56 (s): OH; 6.17 (d)-6.46 (d): H$_1$, H$_2$; 7.25 to 7.43 (m) 6H and 7.64 (m) 4H: SiPh$_2$.

Stage D: 4-chloro-3-[[(2,2-dimethylethyl)(diphenyl)silyl]oxy]11-beta-[4-(3-iodopropoxy)phenyl]-estra-1,3,5(10)-trien-17-one (O-alkylation)

3.18 g of the product obtained in the preceding stage, 15 ml of 1,3-diodopropane, 800 mg of ground soda and 300 mg of tetrabutylammonium bromide, acidified with 2N hydrochloric acid are mixed together for 4 hours at ambient temperature, followed by extraction, washing, drying and evaporating under reduced pressure until the crude product is obtained (39.8 g) which is purified by chromatography eluting with a petroleum ether/ACOET mixture 75/25. 2.43 g of expected pure product is obtained. (Rf: petroleum ether/AcOEt 80/20=0.3).

NMR (CDCl$_3$): 0.41 (s): CH$_3$ in position 18; 1.10 (s): C(CH$_3$)$_3$; 3.34 (t): O—CH$_2$—CH$_2$—I; 3.85 (tl): H$_{11}$; 3.91 (t): O—CH$_2$—CH$_2$—I; 6.16 (d)-6.46 (d): H$_1$, H$_2$; 7.25 to 7.45 6H and 7.66 4H: SiPh$_2$.

Stage E: 4-chloro-3-[[(2,2-dimethylethyl)(diphenyl)silyl]oxy]11-beta-[4-[3-(1-piperidinyl)propoxy]phenyl]-estra-1,3,5(10)-trien-17-one (substitution of the iodine by piperidine)

The operation is carried out as in Stage E of Example 1, starting with the product obtained in the preceding stage. 2.07 g of the expected pure product is obtained (Rf AcOEt/TEA 98/2=0.23).

NMR (CDCl$_3$): 0.42 (s): CH$_3$ in position 18; 1.10 (s): C(CH$_3$)$_3$; 2.52: cyclic CH$_2$—N; 2.83: CH$_2$—N of the chain; 3.84 (tl): H$_{11}$; 3.88 (t): CH$_2$—O; 6.16 (d)-6.47 (d): H$_1$, H$_2$; 6.56–6.80: Ph—O; 7.25–7.40 6H and 7.65 4H: SiPh$_2$.

Stage F: 4-chloro-11beta-[4-[3-(1-piperidinyl)propoxy]phenyl]-estra-1,3,5(10)-triene-3,17-beta-diol (reduction of 17-keto and deprotection)

a) Reduction of 17-keto 63 mg of 97% sodium borohydride is added under an inert gas atmosphere and at ambient temperature to a solution of 600 mg of the product obtained in the preceding stage in 4 ml of methanol and 2 ml of tetrahydrofuran, while cooling the reaction medium down in an ice bath and agitation is carried out for 50 minutes. Ethyl acetate is added followed by washing with salt water, drying and evaporating under reduced pressure until 614 mg of the expected crude product is obtained.

b) Deprotection of the phenol in position 3

1.6 ml of a solution of tetrabutyl ammonium fluoride in tetrahydrofuran is added under an inert gas atmosphere, at ambient temperature to a solution of 614 mg of the product obtained previously in 6 ml of tetrahydrofuran and agitation is carried out for 50 minutes at ambient temperature. The reaction medium is poured into water followed by extraction, washing, drying and evaporating under reduced pressure until 840 mg of crude product is obtained which is purified by chromatography eluting with a dichloromethane/methanol/ammonium hydroxyl mixture 90/10/1. 215 g of expected pure product is obtained.

(Rf CH$_2$Cl$_2$/MeOH/NH$_4$OH 90/10/1=0.3).

NMR (CDCl$_3$): 0.38(s): CH$_3$ in position 18; 2.45 (m): CH$_2$—N; 3.72 (t): H$_{17}$; 3.86: H$_{11}$, CH$_2$—O; 6.61–6.93: Ph—O; 6.61–6.75: H$_1$, H$_2$.

EXAMPLE 6

4-chloro-11beta-[4-[4-(1-piperidinyl)butoxy]phenyl]-estra-1,3,5(10)-triene-3,17-beta-diol The operation is carried out in the same manner as in Example 5, the O-alkylation being carried out:

- either with 4-chloro-1-butanol, by Mitsunobu's reaction in the presence of triphenylphosphine, diethylazodicarboxylate in tetrahydrofuran and the chlorinated product obtained being converted into the iodized product according to the process described in Example 1 Stage D,
- or by direct action with 1,4-diiodobutane (cf Ex. 6). 189 mg of expected pure product is obtained (Rf CH$_2$Cl$_2$/MeOH/NH$_4$OH 90/10/1=0.24).

EXAMPLE 7

4-chloro-11beta-[4-[5-(1-piperidinyl)pentyloxy]phenyl]-estra-1,3,5(10)-triene-3,17-beta-diol The operation is carried out as in Example 5, the O-alkylation is carried out with 1,5-diiodopentane. 125 mg of expected pure product is obtained. (Rf CH$_2$Cl$_2$/MeOH/NH4OH 90/10/1=0.30).

EXAMPLE 8

(17beta) 4-chloro-11beta-[4-[2-(1-piperidinyl)
ethoxy]phenyl]-spiro-[estra-1,3,5(10)-triene-17,2'
(5'H) furan]-3-ol Stage A: (17beta) 4-chloro-11beta-(4-hydroxyphenyl)spiro-[estra-4,9-diene-17,2'(5'H)-furan]-3-one (Chlorination)

4.51 g of N-chloro succinimide is added under an inert atmosphere, at 60° C. to a suspension of 10.46 g of (17beta)-11beta-(4-hydroxy phenyl)-spiro-[estra-4,9-diene-17,2' (5'H)-furan]-3-one (WO 87/05908) in 100 ml of dimethylformamide and the reaction medium is left to react for 10 minutes under agitation. The reaction medium is then poured onto an ice-cooled solution of sodium chloride followed by extracting, drying and evaporating under reduced pressure until 20.85 g of crude product is obtained. 8.93 g of the product obtained in a related trial carried out in an identical manner is added and the whole is purified by chromatography eluting with a $CH_2Cl_2$/acetone mixture 95/5, then recrystallization from ethyl ether. 0.98 g of expected pure product is obtained. (Rf $CH_2Cl_2$/acetone 95/5 0.2). M.p.= 258° C.

Stage B: (17beta)-4-chloro-11beta-[4-(2-bromoethoxy) phenyl]-spiro-[estra-4,9-diene-17,2'(5'H)furan]-3-one The operation is carried out as in Example 1 Stage A, but starting with 1,2-dibromoethane. 5.34 g of expected pure product is obtained. (Rf essence G/AcOEt 75/25=0.21).

Stage C: Aromatization and Saponification
Stage D: Iodization
Stage E: Condensation of the Piperidine Stages C, D and E are carried out in a similar manner to Stages C, D and E of Example 1.

0.657 g of expected pure product is obtained (Rf AcOEt/TEA 92/8=0.21).

NMR ($CDCl_3$): 0.48 (s): $CH_3$ in position 18; 2.47 (m): cyclic $CH_2$—N; 2.70 (t): $CH_2$—N chain; 3.89 (tl): $H_{11}$; 3.99 (t): $CH_2$—O chain; 4.56: $CH_2$—O ring; 5.78: OH; 5.87: H'$_3$, H'$_4$; 6.60–6.80: $H_1$ and $H_2$; 6.60–6.86: Ph—O.

EXAMPLE 9

(17beta) 4-chloro-11beta-[4-[2-(diethylamino)
ethoxy]phenyl]-spiro-[estra-1,3,5(10)-triene-17,2'
(5'H) furan]-3-ol The operation is carried out as in Example 8 but with final condensation of diethylamine on the iodine derivative. 0.512 g of expected pure product is obtained (Rf $CH_2Cl_2$/MeOH/$NH_4OH$ 93/7/0.2=0.29).

NMR ($CDCl_3$): 0.48 (s): $CH_3$ in position 18; 1.03 (t): $CH_2$—$CH_3$; 2.60 (q): $CH_2$—$CH_3$; 2.81 (t): $CH_2$—N; 3.89 (tl): $H_{11}$; 3.93 (t): $CH_2$—O chain; 4.56: $CH_2$—O ring (H'$_3$); 5.87: H'$_3$H'$_4$; 6.61–6.79: $H_1$ and $H_2$; 6.61–6.86: Ph—O.

EXAMPLE 10

(17beta) 4-chloro-11beta-[4-[2-(1-pyrrolidinyl)
ethoxy]phenyl]-spiro-[estra-1,3,5(10)-triene-17,2'
(5'H) furan]-3-ol The operation is carried out as in Example 8 but with final condensation of the pyrrolidine on the iodine derivative. 0.628 g of expected product is obtained.

M.p.=226–227° C. (Rf $CH_2Cl_2$/MeOH/$NH_4OH$ 93/7/0.2= 0.25).

NMR ($CDCl_3$): 0.48 (s): $CH_3$ in position 18; 2.59 (m): cyclic $CH_2$—N; 2.80 (m): $CH_2$—N chain; 3.89 (tl): $H_{11}$; 3.98 (t): $CH_2$—O of the chain; 4.56 (m): cyclic $CH_2$—O (H'$_5$); 5.87 (m): H'$_3$, H'$_4$; 6.60–6.78 (d): $H_1$ and $H_2$; 6.60–6.86 AA'BB': Ph—O.

EXAMPLE 11

(17beta) 4-chloro-11beta-[4-[3-(1-piperidinyl)
propoxy]phenyl]-spiro-[estra-1,3,5(10)-triene-17,2'
(5'H) furan]-3-ol The operation is carried out as in Example 8, the O-alkylation is carried out directly with 1,3-diiodopropane (avoids Stage D of Example 8). 0.591 g of expected pure product is obtained (Rf AcOEt/TEA 92/8=0.19).

NMR ($CDCl_3$): 0.48 (s): $CH_3$ in position 18; 2.30 to 2.50: $CH_2$—N; 3.87 (m): $CH_2$—O chain, $H_{11}$; 4.56: $CH_2O$ ring (H'$_5$); 5.88: H'$_3$, H'$_4$; 6.61–6.79: $H_1$ and $H_2$; 6.61–6.86: Ph—O.

EXAMPLE 12

(17beta) 4-chloro-11beta-[4-[4-(1-piperidinyl)
butoxy]phenyl]-spiro-[estra-1,3,5(10)-triene-17,2'
(5'H) furan]-3-ol The operation is carried out as in Example 8 Stages A, B, C, D, E, the O-alkylation is carried out with 1-bromo-4-chlorobutane. 0.494 g of pure product is obtained. Rf AcOEt/TEA 95/5=0.22 M.p.=154° C.

NMR ($CDCl_3$): 0.50 (s): $CH_3$ in position 18; 2.36 (6H): C$H_2$—N ring, chain; 3.85 (t): $CH_2$—O; 3.89 (t): $H_{11}$; 4.57 (s): cyclic $CH_2$—O (H'$_5$); 6.60 (m) (3H)-6.86 (m) (2H): Ph—O and $H_2$; 6.79(d): $H_1$.

EXAMPLE 13

4-chloro-3-hydroxy-11beta-[4-[2-(1-dimethyl-
amino)ethoxy]phenyl]-estra-1,3,5(10)-trien-17-one Stage A: 4-chloro-11beta-[4-[2-(dimethylamino)ethoxy] phenyl]-estra-4,9-diene-3,17-dione (introduction of 4-chloro)

6 ml of sulphuryl chloride at 10% in dichloromethane is added under an inert atmosphere, at ambient temperature to a solution of 1.08 g of 11β-[4-[2-(dimethylamino)ethoxy] phenyl]-estra-4,9-diene-3,17-dione in 11 ml of pyridine and agitation is carried out for 30 minutes at approximately −36° C. The reaction medium is poured into sodium bicarbonate, followed by extraction, washing, drying and evaporating under reduced pressure until 1.84 g of crude product is obtained, which is purified by chromatography, eluting with an ethyl acetate/triethylamihe mixture 80/20. 616 mg of expected pure product is obtained. (Rf AcOEt/TEA 8/2= 0.35).

Stage B: 4-chloro-11beta-[4-[2-(dimethylamino)ethoxy] phenyl]-3-hydroxy-estra-1,3,5(1)-trien-17-one (Aromatization and Saponification)

The aromatization reaction, then the saponification reaction are carried out as in Example 1, Stage C, starting with 700 mg of the product obtained in the preceding stage. 360 mg of expected pure product is obtained. M.p.=254° C. (Rf $CH_2Cl_2$/iPrOH/$NH_4OH$ 93/7/0.7=0.18).

NMR ($CDCl_3$): 0.44 (s): $CH_3$ in position 18; 2.30 (s): NMe2; 2.67 (m): $CH_2$—N; 3.94 (m): $CH_2$—O; 4.00: $H_{111}$; 6.62–6.91: Ph—O; 6.62–6.81 (d): $H_1$, $H_2$.

The compound of Example 3 was prepared in the same manner.

EXAMPLE 14 gamma lactone of 4-chloro-3,17beta-dihydroxy-
11beta-[4-[2-(1-pyrrolidinyl)ethoxy]phenyl]-19-nor-
17alpha-pregna-1,3,5(10)-triene-21-carboxylic acid 6 ml of tetrahydrofuran/siliporite is added under an inert atmosphere, at ambient temperature to 5.93 ml of n-butyllithium at 15% in hexane, then at −50° C., 0.921 g of allyl bis-dimethylamido phosphate in solution in tetrahydrofuran is added and finally at −30° C. 0.586 g of the product obtained in Example 2 is added and the reaction medium is agitated for 1 hour 45 minutes at ambient temperature.

8 ml of 2N hydrochloric acid and 50 ml of a saturated solution of sodium bicarbonate are added followed by extraction, washing, drying and evaporating under reduced pressure until 0.590 g of crude product is obtained which is purified by chromatography eluting with an ethyl acetate/triethylamine mixture 60/40, then recrystallization from isobutanol. 0.162 g of expected pure product is obtained. M.p.=231° C. Rf AcOEt/TEA 60/40 =0.20.

NMR (CDCl$_3$): 0.51 (s): CH$_3$ in position 18; 1.79 (m): CH$_2$ in beta position of N ring; 2.58 (m): CH$_2$ in alpha position of N ring; 2.83 (t): CH$_2$—N of the chain; 3.99 (t): CH$_2$—OAr; 3.99 (t): H$_{11}$; 6.62: H$_2$; 6.82: H$_1$; 6.62: ArO; 6.82: ArC.

EXAMPLE 15 gamma lactone of 4-chloro-3,17beta-dihydroxy-11beta-[4-[2-(1-piperidinyl)ethoxy]phenyl]-19-nor-17alpha-pregna-1,3,5(10)-triene-21-carboxylic acid The operation is carried out as in as in Example 14, but starting with 1.179 g of the product of Example 1. 0.388 g of the expected pure product is obtained. (Rf CH$_2$Cl$_2$/iPrOH/NH4OH (95/5/0.5=0.20)).

NMR (CDCl$_3$): 0.52 (s): CH$_3$ in position 18; 2.50 (m): cyclic CH$_2$ N; 2.71 (t): CH$_2$—N of the chain; 4.00 (t): CH$_2$—OAr; 4.00 (t masked): H$_{11}$; 6.62: H$_2$; 6.81: H$_1$; 6.62: ArO; 6.85: ArC.

EXAMPLE 16 gamma lactone of 4-chloro-3,17beta-dihydroxy-11beta-[4-[2-(diethylamino)ethoxy]phenyl]-19-nor-17alpha pregna-1,3,5(10)-triene-21-carboxylic acid The operation is carried out as in as in Example 14, but starting with 0.428 g of the product of Example 3. 0.195 g expected pure product is obtained. (Rf AcOEt/TEA/Essence G (50/30/20=0.25))

NMR (CDCl$_3$): 0.51 (s): CH$_3$ in position 18; 1.03 (t): N-CH$_2$—C$\underline{H}_3$; 2.60 (q): N—C$\underline{H}_2$—CH$_3$; 2.81 (t): CH$_2$—N of the chain; 3.94 (t): C$\underline{H}_2$—O—Ar; 3.98 (t): H$_{11}$; 6.59: H$_2$; 6.79: H$_1$; 6.59: ArO; 6.85: ArC.

EXAMPLE 17 gamma lactone of (17-alpha)-4-chloro-3,17beta-dihydroxy-11beta-[4-[3-(1-piperidinyl)propoxy]phenyl]-19-nor-pregna-1,3,5(10)-triene-21-carboxylic acid Stage A Lactonization The operation is carried out as in Example 14, but starting with 1.44 g of the compound of Example 5 Stage E. 2.36 g of crude product is obtained which is used directly in the deprotection reaction of the phenol in position 3.

Stage B: Deprotection of the Phenol in Position 3

3.8 ml of a solution of tetrabutyl ammonium fluoride in tetrahydrofuran is added to absolution of 2.36 g of the product obtained in the preceding stage in 24 ml of tetrahydrofuran and agitation is carried out for 50 minutes at ambient temperature. The reaction medium is poured into water followed by extraction, drying and evaporating under reduced pressure until 695 mg of crude product is obtained which is purified by chromatography eluting with a dichloromethane/methanol mixture 93/7, then by recrystallization. 238 mg of expected pure product is obtained. M.p. 242° C. Rf CH$_2$Cl$_2$/MeOH/NH4OH 93/7/0.7=0.28.

NMR (CDCl$_3$): 0.51 (s): CH$_3$ in position 18; 2.30 to 2.60: CH$_2$—N; 3.88: CH$_2$O; 3.98 (tl): H$_{11}$; 6.61, 6.87: Ar—O, Ar—C; 6.61–6.76: H$_1$, H$_2$.

EXAMPLE 18 gamma lactone of 4-chloro-3,17beta-dihydroxy-11beta-[4-[4-(1-piperidinyl)butoxy]phenyl]-19-nor-17alpha-pregna-1,3,5(10)-triene-21-carboxylic acid The operation is carried out as in Example 17, but starting with 1.2 g of the product of Example 6 Stage E. 310 mg of expected pure product is obtained (Rf CH$_2$Cl$_2$/MeOH/NH$_4$OH 95/5/0.5=0.17).

NMR (CDCl$_3$): 0.51 (s): CH$_3$ in position 18; 3.83 (t): CH$_2$—O chain; 3.99 (tl): H$_{11}$; 6.61–6.85: Ar—O, Ar—C; 6.61–6.79: H$_1$, H$_2$.

EXAMPLE 19 gamma lactone of 4-chloro-3,17beta-dihydroxy-11beta-[4-[5-(1-piperidinyl)pentyloxy]phenyl]-19-nor-17alpha-pregna-1,3,5(10)-triene-21-carboxylic acid The operation is carried out as in Example 17, but starting with 1.44 g of the product of Example 7 Stage E. 330 mg of expected pure product is obtained (Rf AcOEt/TEA 90/10= 0.22).

NMR (CDCl$_3$): 0.52 (s): CH$_3$; 3.83 (t): CH$_2$—O; 3.99 (t): H$_{11}$; 6.60 (m) 3H, 6.67 (d) H$_1$, 6.85 (d) 2H: Aromatic H$_1$, H$_2$.

EXAMPLE 20

4-chloro-11beta-[4-[2-(diethylamino)ethoxy]phenyl]-estra-1,3,5 (10)-triene-3,17beta-diol 37 mg of sodium borohydride is added under an inert atmosphere to a solution of 241 mg of the compound of Example 3, in 4 ml of methanol, agitation is carried out for 1 hour in an ice bath, then 2 ml of hydrochloric acid is added then the reaction medium is poured into an aqueous solution of sodium bicarbonate, followed by extraction with ethyl acetate, washing, drying and evaporating under reduced pressure until 245 mg of crude product is obtained which is purified by chromatography eluting with a dichloromethane/methanol/ammonium hydroxide mixture 90/10/1. 195 mg of expected pure product is obtained. Rf CH$_2$Cl$_2$/MeOH/NH$_4$OH 90/10/1=0.27.

NMR (CDCl$_3$): 0.32 (s): CH$_3$; 1.03 (t): CH$_2$C$\underline{H}_3$; 2.60 (q): C$\underline{H}_2$CH$_3$; 2.81 (t): CH$_2$—N; 3.68: H17; 3.93 (t): CH$_2$—O; 6.62: ArO; 6.89: ArC; 6.80 (d): H$_1$: 6.62 (d): H$_2$.

In a similar manner to Example 20, the following products of formula (I') are obtained with R'$_5$=OH and R'$_6$=H:

|  | Starting product | n' | X' | NR'$_3$R'$_4$ | Rf s. |
|---|---|---|---|---|---|
| Ex. 21 | Ex. 4 | 2 | Br | Piperidino | 0.45 AcOEt/TEA 90/10 |
| Ex. 22 | Ex. 1 | 2 | Cl | Piperidino | 0.13 AcOEt/TEA 95/5 |

-continued

| | Starting product | n' | X' | NR'$_3$R'$_4$ | Rf s. |
|---|---|---|---|---|---|
| Ex. 23 | Ex. 2 | 2 | Cl | Piperidino | 0.13 CH$_2$Cl$_2$/MeOH NH$_4$OH 93/7/0.5 |
| Ex. 24 | Ex. 13 | 2 | Cl | NMe$_2$ | 0.25 CH$_2$Cl$_2$/iPrOH/ NH$_4$OH 90/10/1 |

EXAMPLE 25

4-chloro-11beta-[4-[2-(diethylamino)ethoxy]phenyl]-19-nor-17alpha-pregna-1,3,5(10)-trien-20-yne-3,17beta-diol 4.7 ml of a 0.43 M/l solution of potassium acetylide is added under an inert atmosphere to a solution of 250 mg of the product of Example 3 in 3 ml of tetrahydrofuran/siliporite, agitation is carried out for 1 hour at ambient temperature, then 4 ml of hydrochloric acid is added. The reaction medium is poured into a saturated aqueous solution of sodium bicarbonate followed by extraction, washing, drying and evaporating under reduced pressure until 260 mg of crude product is obtained which is purified by chromatography eluting with a CH$_2$Cl$_2$/MeOH/NH$_4$OH mixture 90/10/0.5. 215 mg of expected pure product is obtained. Rf CH$_2$Cl$_2$/MeOH/NH$_4$OH 90/10/0.5=0.31.

NMR (CDCl$_3$): 0.43 (s): CH$_3$ in position 18; 1.04 (t): CH$_2$C$\underline{H}$$_3$; 2.62 (q): C$\underline{H}$$_2$CH$_3$; 2.64 (s): C≡C—H; 2.83 (t): CH$_2$—N; 3.95 (t): CH$_2$—O; 4.00 (tl): H$_{11}$; 6.62: Ph—O; 6.90: Ph—C; 6.82 (d): H$_1$; 6.62 (d): H$_2$.

EXAMPLE 26

(17beta)-4-chloro-4',5'-dihydro-11beta-[4-[2-(1-piperidinyl)ethoxy]phenyl]-spiro[estra-1,3,5(10)-triene-17,2'-(3'H)-furan]-3-ol 0.041 g of 9.5% Pd/C catalyst is added to a solution of 0.411 g of the product of Example 8 in 15 ml of ethanol and 5 ml of tetrahydrofuran and hydrogenation is carriedout for 2 hours 30 minutes (vol. of H$_2$ absorbed 17.5 cm$^3$). After filtration of the catalyst, evaporation is carried out under reduced pressure until 0.42 g de crude product is obtained which is purified by chromatography eluting with an ethyl acetate/triethylamine mixture 92/8. 0.33 g of expected pure product is obtained. M.p. 170° C. Rf AcOEt/TEA 92/8=0.21.

In a similar manner to Example 26, the following products of formula (I') are obtained, in which R'$_3$ and R'$_6$ form together with the carbon that carries them the saturated ring

| | Starting product | n' | X' | NR'$_3$R'$_4$ | Rf s. |
|---|---|---|---|---|---|
| Ex. 27 | Ex. 11 | 3 | Cl | Piperidino | 0.19 AcOEt/TEA 92/8 |
| Ex. 28 | Ex. 12 | 4 | Cl | Piperidino | 0.22 AcOEt/TEA 95/5 |

EXAMPLE 29

4-chloro-11β-[4-[2-(diethylamino)ethoxy]phenyl]-17alpha-methyl-estra-1,3,5(10)-triene-3,17beta-diol a) Preparation of "Cerium Compound"

24 ml of anhydrous THF is added to 2.42 g of CeCl$_3$-7H$_2$O, dried beforehand under reduced pressure at 140° C. for 2 hours, then put under an inert atmosphere, the suspension is agitated for 2 hours, cooled down to −78° C. and 4.35 ml of CH$_3$Li in ether is added and agitation is carried out for 30 minutes at −78° C.

b) Condensation 0.644 g of the compound prepared in Example 3 in solution in 8.5 ml of anhydrous THF is added at −78° C. and the reaction medium is maintained at this temperature for one hour. The reaction medium is poured into 25 ml of a saturated solution of NH$_4$Cl followed by extraction, washing, drying and evaporating under reduced pressure until 0.599 g of crude product is obtained which is purified by chromatography (after having added 0.192 g of crude product obtained during a related trial carried out in an identical manner) eluting with a CH$_2$Cl$_2$/CH$_3$OH/NH$_4$OH mixture (92/8/0.2), then with an AcOEt/TEA mixture (87/13). 0.402 g of expected pure product is obtained. Rf CH$_2$Cl$_2$/MeOH/NH$_4$OH (92/8/0.2)=0.18 M.p.=161–163° C.

NMR (CDCl$_3$): 0.44 (s): CH$_3$ in position 18; 1.28 (s): CH$_3$ in position 17; 1.03 (t): CH$_2$C$\underline{H}$$_3$; 2.61 (q): C$\underline{H}$$_2$13 CH$_3$; 2.81 (t): CH$_2$—N;. 3.94 (t): C$\underline{H}$$_2$—O; 3.96: H$_{11}$; 6.61–6.80: H$_1$ and H$_2$; 6.61–6.83: Ph—O.

EXAMPLE 30

4-chloro-17alpha-methyl-11β-[4-[2-(1-piperidinyl)ethoxy]phenyl]-estra-1,3,5(10)-triene-3,17beta-diol The operation is carried out as in Example 28, but starting with 2.79 g of the product obtained in Example 1.

2.12 g of expected pure product is obtained. Rf CH$_2$Cl$_2$/CH$_3$OH/NH$_4$OH (93/7/0.2)=0.19 M.p.=163° C.

NMR (CDCl$_3$): 0.44.(s): CH$_3$ in position 18; 1.28 (s): CH$_3$ in position 17; 2.48. (tl) 4H: CH2N ring; 2.71 (t): CH$_2$—N chain; 3.99 (t): C$\underline{H}$$_2$—O;=4.00 masked: H$_{11}$; 6.80 (d): H$_1$; 6.98 (d): H$_2$; 6.60–6,88: Ph—O.

| EX | X | n | R₁ | Y | NR₃R₄ | R₅ | R₆ | Rf | |
|----|----|---|----|---|-------|----|----|----|---|
| 31 | Cl | 2 | H | O |  | OH | Me | (a) 90/10/0,4 | 0,25 |
| 32 | Cl | 2 | H | O |  | OH | Me | (a) 90/10/0,9 | 0,25 |
| 33 | Cl | 2 | H | O |  | OH | H | (a) 90/10/1 | 0,26 |
| 34 | Cl | 2 | H | O | NMeiPr | OH | H | (a) 90/10/0,5 | 0,22 |
| 35 | Cl | 2 | H | O |  | OH | H | (b) 30/70 | 0,22 |
| 36 | Cl | 2 | H | O | NEtPr | OH | H | (a) 90/10/0,5 | 0,27 |
| 37 | Cl | 2 | H | O | NMeEt | OH | H | (b) 30/70 | 0,22 |
| 38 | Cl | 2 | H | O | 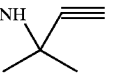 | OH | H | (a) 95/5/0,5 | 0,28 |
| 39 | Cl | 2 | H | O |  | OH | H | (b) 30/70 | 0,33 |
| 40 | Cl | 2 | H | O | 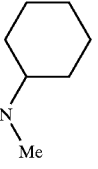 | OH | H | (b) 30/70 | 0,32 |
| 41 | Cl | 2 | H | O | NEtBu | OH | H | (a) 90/10/0,5 | 0,37 |
| 42 | Cl | 2 | H | O |  | OH | H | (a) 90/10/0,5 | 0,20 |
| 43 | Cl | 2 | H | O |  | CH | H | (a) 95/5/0,5 | 0,25 |
| 44 | Cl | 2 | H | O | 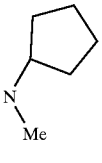 | CH | H | (a) 90/10/0,5 | 0,30 |
| 45 | Cl | 2 | H | O | NPr₂ | OH | H | (a) 95/5/0,5 | 0,20 |
| 46 | Cl | 2 | H | O |  | CH | H | (b) 30/70 | 0,28 |
| 47 | Cl | 2 | H | O | NEtiPr | OH | H | (a) 90/10/0,5 | 0,22 |
| 48 | Cl | 2 | H | O | NMePr | OH | H | (a) 90/10/0,5 | 0,22 |
| 49 | Cl | 2 | H | O | NMeBu | OH | H | (a) 90/10/0,5 | 0,22 |
| 50 | Cl | 2 | H | O | 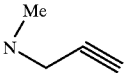 | OH | H | (a) 95/5/0,5 | 0,22 |

-continued

| EX | X | n | R₁ | Y | NR₃R₄ | R₅ | R₆ | Rf | |
|---|---|---|---|---|---|---|---|---|---|
| 51 | Cl | 2 | H | O | 4-methylpiperidin-1-yl | OH | H | (a) 90/10/0,5 | 0,32 |
| 52 | Cl | 2 | H | S | piperidin-1-yl | OH | H | (a) 93/7/0,5 | 0,30 |
| 53 | Cl | 2 | H | SO | piperidin-1-yl | OH | H | (a) 93/7/0,5 | 0,23 |
| 54 | Cl | 2 | (CH₂)₃—COOH | O | NEt₂ | CH | H | (a) 80/20/1 | 0,25 |
| 55 | Cl | 2 | H | O | piperidin-1-yl | =N—OH | | (a) 90/10/0,5 | 0,18 |
| 56 | Cl | 2 | H | O | N(Et)CH₂CH₂COOH | OH | H | | |

(a) CH₂Cl₂/MeOH/NH₄OH
(b) TEA/AcOEt

Pharmacological Tests
Effect on the Proliferation of Mammary Cells

The proliferative activity of the molecules is studied in comparison to that of oestradiol on MCF-7 human mammary cells in culture.

In order to reveal an agonist effect of the oestradiol and/or the tested molecules, the cell maintenance culture (rich in growth factors and steroids) is replaced by an impoverished medium, amongst others free of steroids (DMEM supplemented with 5% of steroid-free serum and without phenol red). Cells undergo this severance two days before the start of the test.

After 7 days culture in the presence of the products to be studied, the cell proliferation is evaluated by determination of the DNA. In each test, the effect of the oestradiol at $10^{-10}$M (cell growth in the presence of oestradiol less cell growth in the presence of the solvent) determines the 100% agonist activity. The activity of the molecules is evaluated in comparison to this internal control. The molecules inducing an identical cell growth to that observed with the solvent alone are classified as "inactive", those inducing a lower cell growth to that observed with the solvent are classified as "inhibitor".

| | ACTIVITY |
|---|---|
| Oestradiol | Agonist |
| Example 20 | Mixed* |
| Example 22 | Inactive |
| Example 23 | Mixed |
| Example 1 | Mixed |
| Example 30 | Mixed |

*Mixed: slight agonist activity at very low concentrations and an inhibitory activity at higher concentrations.

Bone impact study of a product in the ovariectomized female rat at the age of 3 months Compounds A, B, C, D, E are tested in order to determine their effect on the bone mass and on the formation and resorption activity in the model of the ovariectomized rat at the age of 3 months. The animals are treated in a preventive fashion.

| Animals: | |
|---|---|
| Species | rat |
| Strain | Sprague-Dawley |
| Sex | female |
| Weight | 250 g to 280 g |
| No. of animals/group | 8 |

Products
1—Product to be tested: Products of Examples 20, 22, 23, 30 and 1.
   vehicle(s): corn oil, 0.5% methylcellulose
   dose(s): one dose per tested product (0.3 mg/kg/d)
   number of administrations: once/day; 5 days/week for 4 weeks
   administration route: oral route for the products
   volumes: 5 ml/kg (p.o.)
   period between the last injection and sacrifice: 24 hours
   number of administrations: 20.
2—Reference product: 17β oestradiol is administered by subcutaneous route at a dose of 0.1 mg/kg/d in solution in a mixture of corn oil-benzyl alcohol (99:1, v/v) under a volume of 0.2 ml/kg.

Experimental Protocol
Animals

The study is carried out with female rats ovariectomized at the age of 3 months. The animals are kept in an air conditioned room (temperature 20° C.±2° C.) and grouped by 4 into boxes. The animals receive, ad libitum, demineralized water and compressed foods (pellets: AO4CR-10 UAR).

Surgery

The 3 month old female rats weighing approximately 250 g are ovariectomized under anaesthesia with Imalgene 1000, at a dose of 100 mg/kg by intraperitoneal route (i.p.) and under a volume of 1 ml/kg. They also receive Nembutal (3 mg/kg i.p. under a volume of 0.3 ml/kg).

After lateral incision, cutaneous and muscular planes are sectioned. The exeresis of each ovary is carried out after ligature of the oviduct.

The "SHAM" control rats are anaesthetised under the same conditions. After incision of the cutaneous and muscular planes, each ovary is exposed then replaced in situ.

Treatment

The effects of the products are determined in a preventive treatment. They are administered immediately after the ovariectomy. Animals distributed into groups of 8.

Group 1: "SHAM" control rats receiving the vehicle or vehicles

Group 2: "OVX" control rats receiving the vehicle or vehicles.

Groups X: "OVX" rats receiving respectively defined doses of the product or products to be tested.

Blood Samples

At the end of 4 weeks (duration of the study) the animals are decapitated by guillotine. The serums collected after centrifugation are preserved at −20° C.

A lipidic balance will be established from the serous determinations of total cholesterol, of triglycerides and of phospholipids on a 500 μl aliquot of serum. The lowering of the seric cholesterol level is expressed in % relative to the level shown by the ovariectomized animals receiving only the solvent.

Organ Samples

After sacrificing the animals, the following organs are removed:

tractus genitalis

The uteri are removed. The latter are weighed. The increase in weight is expressed in % of the weight of the uterus of ovariectomized animals receiving only the solvent.

at the bone level:

The bone mass (BMD or Bone mineral density) is measured by biphotonic dual energy X-ray absorptiometry (DEXA). The measurements are carried out on bone excized and cleaned of all soft tissue. The BMD (Bone mineral density) is measured on the whole bone as well as on the metaphyseal part at the level of the proximal extremity for the left tibia. This zone is defined as being the region which is richest in trabecular bone; and consequently, is the most sensitive to variations in bone volume and bone mineral density.

The results are expressed in % according to the formula:

$$\frac{\text{Tested product } BMD - OVX\ BMD}{SHAM\ BMD - OVX\ BMD} \times 100$$

|  | Dose Route mg/kg | TIBIA BONE BMD % | UTERUS Weight % | Cholesterol % |
|---|---|---|---|---|
| OVX |  | 0 |  |  |
| SHAM |  | 100 |  |  |
| Oestradiol | 0.1 s.c. | 105 | 359 | −35 |
| Ex. 20 | 0.3 po | 69 | 60 | −43 |
| Ex. 20 | 1.0 po | 74 | 50 | −40 |
| Ex. 22 | 0.3 po | 63 | 57 | −52 |
| Ex. 23 | 0.3 po | 67 | 64 | −53 |
| Ex. 23 | 1.0 po | 71 | 74 | −53 |
| Ex. 1 | 0.3 po | 57 | 55 | −50 |
| Ex. 1 | 1.0 po | 64 | 55 | −48 |
| Ex. 30 | 0.3 po | 52 | 68 | −51 |
| Ex. 30 | 1.0 po | 71 | 55 | −48 |

What is claimed is:

1. A compound selected from the group consisting of a compound of the formula

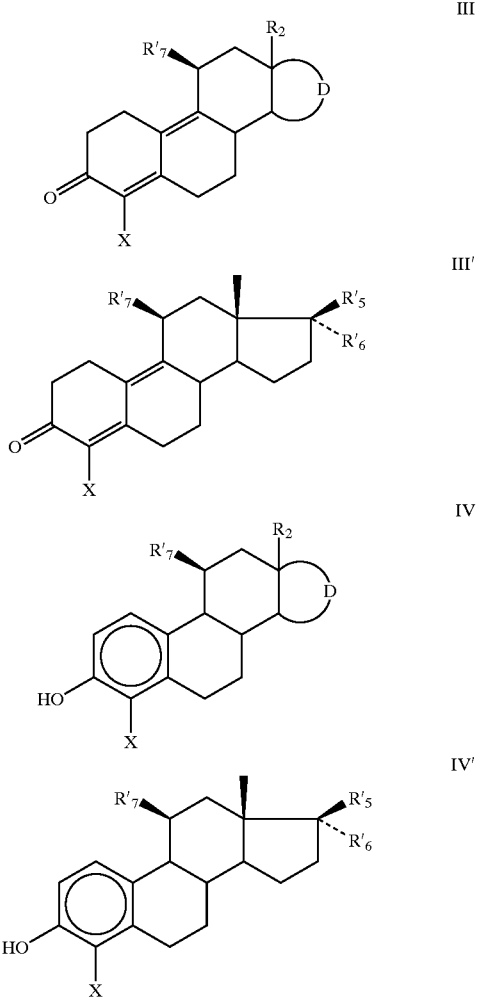

wherein X is halogen, $R_2$ is unsaturated or saturated hydrocarbon of 1 to 6 carbon atoms, D is the remainder of an unsaturated or saturated pentagonal or hexagonal ring unsubstututed or substituted with at least one member of the group consisting of —OH, —O—$(CH_2)_m$—Alk, —OCO—Alk, —O—$(CH_2)_m$—Ar, —O—COAr, —O—$(CH_2)_m$—

Het, —OCO—Het, alkyl of 1 to 6 carbon atoms, alkenyl of 2 to 6 carbon atoms alkynyl of 2 to 6 carbon atoms,

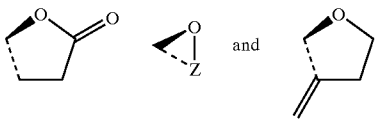

m is an integer from 0 to 3, Z is —(CH$_2$)$_1$— or —CH═CH—(CH$_2$)$_1$, 1 is 1 to 4, 1' is 1 or 2, Alk is unsaturated or saturated alkyl or cycloalkyl of up to 12 carbon atoms, Ar is carbocyclic aryl of 6 to 18 carbon atoms, Het is unsaturated or saturated, aromatic or non-aromatic heterocyclic of 1 to 9 carbon atoms and 1 to 5 hetero atoms selected from the group consisting of oxygen, nitrogen and sulfur, R'$_7$ is selected from the group consisting of

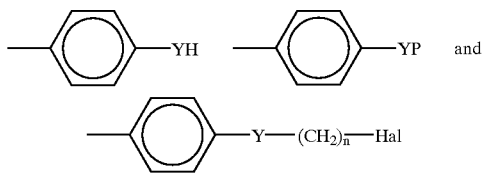

n is an integer from 2 to 8, Hal is halogen, P is a protective group, Y is selected from the group consisting of —O—, —S—, —SO—, —SO$_2$— and —NH—, R$_3$ and R$_4$ are individually selected from the group consisting of hydrogen, —(CH$_2$)$_m$—Ar, —(CH$_2$)$_m$—Het and —(CH$_2$)$_m$—Alk or taken together with the nitrogen form an unsaturated or saturated, aromatic or non-aromatic mono or polycyclic heterocycle of 3 to 15 members containing 1 to 3 heteroatoms selected from the group consisting of oxygen, sulfur and nitrogen, R'$_5$ is selected from the group consisting of —OH, —O—(CH$_2$)$_m$—Alk, —O—CO—Alk, —O—(CH$_2$)$_m$—Ar, —O—CO—Ar, —O—(CH$_2$)$_m$—Het and —O—CO—Het and R'$_6$ is selected from the group consisting of hydrogen, alkyl of 1 to 6 carbon atoms and alkenyl and alkynyl of 2 to 6 carbon atoms, or R'$_5$ and R'$_6$ form oxo or ═NOH or together with the carbon form a member selected from the group consisting of

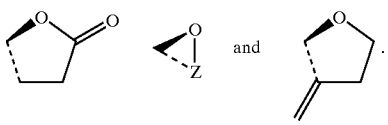

2. A compound of claim 1 wherein D is a pentagonal ring.

3. A compound of claim 1 wherein D is

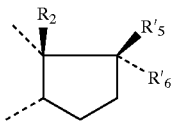

wherein R$_2$ is defined as in claim 1, R$_3$ is selected from the group consisting of —(CH$_2$)$_m$—Alk and —(CH$_2$)$_m$—Het and R$_6$ is selected from the group consisting of hydrogen, alkyl of 1 to 6 carbon atoms and alkenyl and alkynyl of 2 to 6 carbon atoms, m, Alk, and Het are defined as in claim 1 or R'$_5$ and R'$_6$ together form oxo or together with the carbon atom form one of the following

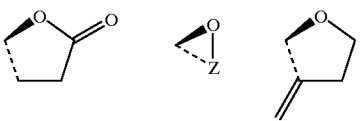

Z is —(CH$_2$)l or —CH═CH—(CH$_2$)l', l is an integer from 1 to 4 and l' is 1 or 2.

* * * * *